ically to the polymer (poly-$\epsilon$-caprolactone) used in the instant invention.

United States Patent [19]
Gregory

[11] 4,186,190
[45] Jan. 29, 1980

[54] METHOD OF TREATING BURNS USING A POLY-$\epsilon$-CAPROLACTONE

[75] Inventor: John B. Gregory, Wayland, Mass.

[73] Assignee: The United States of America as represented by the Secretary of the Navy, Washington, D.C.

[21] Appl. No.: 959,952

[22] Filed: Nov. 13, 1978

[51] Int. Cl.² ............................................. A61K 31/74
[52] U.S. Cl. .............................. 424/78; 424/DIG. 13
[58] Field of Search ........................... 424/78, DIG. 13

[56] References Cited

U.S. PATENT DOCUMENTS

| | | | |
|---|---|---|---|
| 2,542,897 | 2/1951 | Brown et al. | 424/78 |
| 2,693,438 | 11/1954 | Ward | 424/78 |
| 2,804,073 | 8/1957 | Gallienne et al. | 128/156 |
| 3,577,516 | 5/1971 | Gould et al. | 424/46 |
| 3,930,000 | 12/1975 | Margraf | 424/245 |
| 3,935,308 | 1/1976 | Wise et al. | 424/78 |
| 3,983,209 | 9/1976 | Schmitt | 424/78 |

OTHER PUBLICATIONS

The Condensed Chemical Dictionary, 8th ed., 1971, pp. 822, 890 & 891.
Chemical Abstracts, 85:51752j (1976).
Merck Index, 9th ed., 1976, pp. 1232 & 9275.

*Primary Examiner*—Leonard Schenkman
*Attorney, Agent, or Firm*—R. S. Sciascia; W. Thom Skeer; L. E. K. Pohl

[57] ABSTRACT

Composition and method for emergency treatment of burn injuries. A solution of poly-$\epsilon$-caprolactone and triethyl citrate plasticizer or triacetin plasticizer in a volatile solvent such as methylene chloride is applied to the burn area by spraying or swabbing. Upon evaporation of the solvent a flexible film of the plasticized polymer is left to serve as a partial barrier to water loss.

6 Claims, No Drawings

METHOD OF TREATING BURNS USING A POLY-ε-CAPROLACTONE

BACKGROUND OF THE INVENTION

1. Field of the Invention

This invention relates to the treatment of burn wounds.

2. Description of the Prior Art

Shock is the major cause of death in the period following a severe burn over large portions of the body. The primary cause of shock has been recognized as due to the excessive loss of body fluids and proteins through the burned areas. This loss occurs primarily through evaporation and the process is not visable or otherwise readily detectable to the burned party or observer. The loss is therefore called "insensible" even though the results are dramatically apparent.

Many, if not most, burn accidents occur under circumstances which make it impossible for the victim to receive immediate supportive treatment in a hospital. Such is the case, for example, when accidents occur in remote areas such as at sea. Accordingly, there has long been a need for a suitable, readily available, and easily applied burn treatment composition which can be administered by a relatively unskilled person at the scene of the injury.

In the past, various creams, greases, sprays and the like designed to soothe and protect the wound have been applied immediately following the burn as a first aid treatment. In general these have been ineffective in stopping insensible fluid and protein loss through the burn site and have been difficult to apply.

In addition, various converyings for burns and similar wounds which require coverage of a substantial area for an extended period of time have existed. These coverings assist in the skin regeneration and healing processes. They have included skin grafts where the skin was obtained from another person, an animal or from another area of the injured person. Also, various foams, gels, foils and webs of fabrics made from various synthetic plastic materials, animal collagen and the like have been used. Burn wound coverings comprising foams, gels, foils or webs of collagen, or other moist, conformable dressings require special storage techniques which render them impractical for use in remote, isolated places or limited facilities.

In addition, various polymers have been used as burn treatment. For example, vinyl and vinylacetate copolymers have been used as burn coverings. These prior art burn treatment preparations have produced totally impermeable water barriers which allow the collection of fluids below the burn site. This is undesirable. The disadvantages of the prior art burn treatment preparation have led to the use of films of poly-ε-caprolactone as described in U.S. Pat. No. 3,935,308. Poly-ε-caprolactone films have shown great promise in burn treatment but still present some problems insofar as water retention and lack of flexibility are concerned.

SUMMARY OF THE INVENTION

The present invention overcomes the disadvantages associated with the use of poly-ε-caprolactone by means of a plasticizer. Addition of the plasticizer to a solution of poly-ε-caprolactone renders the film formed when the poly-ε-caprolactone is applied significantly more flexible, allows greater adhesion to the burn and produces an improved rate of healing in severe burn cases. The plasticizer must be bio-compatable and produce no toxic effects.

DESCRIPTION OF THE PREFERRED EMBODIMENT

This invention utilizes a solution of poly-ε-caprolactone and a plasticizer in a suitable solvent which can be applied directly to a burned area by means of swab or spray. Poly-ε-caprolactone having a molecular weight in the range of from 2,000 to 300,000 is used. When the solution is spread over a burn wound, the solvent evaporates leaving a 0.001 to 0.01 inch thick, flexible film. The film replaces the destroyed natural keratin moisture barrier and controls the amount of water which can evaporate from the burned area. Once the victim reaches a burn treatment center, the film can be removed and traditional burn treatment begun.

A methylene chloride-methyl acetate mixture is suitable for use as a solvent. Either triethyl citrate or triacetin may be used as the plasticizer.

EXAMPLE

A nonplasticized solution of poly-ε-caprolactone was formulated utilizing 100 grams of poly-ε-caprolactone, 300 ml. of methyl acetate and 200 ml. of methylene chloride. A plasticized solution was also formulated utilizing 100 grams of poly-ε-caprolactone, 33 grams of triethyl citrate, 1200 ml. of methyl acetate and 300 ml. of methylene chloride. Experimental burns were obtained by pressing a 2.22 inch diameter iron heated to 65° against the shaven flanks of pigs. The burned areas were then treated by brushing on one of the solutions. When pigs were treated with the non-plasticized coating, the coating peeled from the burn area within a few days and was only marginally effective. When pigs were treated with the plasticized solution the coating adhered well and the burns healed better than those coated with the non-plasticized solution. Improved healing was particularly significant when the burn was borderline between second and third degree.

Other tests showed that triacetin could be used in lieu of triethyl citrate as the plasticizer. Triacetin may be used in quantities similar to that specified for triethyl citrate above.

What is claimed is:

1. A method for treating a burn wound comprising the steps of:
   A. applying a solution containing about 100 parts by weight of a poly-ε-caprolactone having a molecular weight in the range of from 2000 to 300,000 and about 33 parts by weight of a plasticizer selected from the group consisting of triethyl citrate and triacetin dissolved in a methyl acetate-methylene chloride mixture to the burn wound; and
   B. allowing said methyl acetate-methylene chloride mixture to evaporate.

2. A method according to claim 1 wherein said plasticizer is triethyl citrate.

3. A method according to claim 1 wherein said plasticizer is triacetin.

4. A method according to claim 2 wherein there are 100 g of poly-ε-caprolactone and 33 g of plasticizer per 1200 ml. of methyl acetate and 300 ml of methylene chloride.

5. A method according to claim 4 wherein said plasticizer is triethyl citrate.

6. A method according to claim 4 wherein aid plasticizer is triacetin.

* * * * *